United States Patent
Schwab et al.

(10) Patent No.: US 6,376,255 B1
(45) Date of Patent: Apr. 23, 2002

(54) APPARATUS AND METHOD FOR ANALYZING THE AMOUNT OF CHEMICAL SUBSTRATES IN A LIQUID

(75) Inventors: Ulrich Schwab, Graefelfing; Raimund Essel, Weilheim; Albert Saeuble, Hohenpeissenberg; Rudolf Schumacher, Peissenberg, all of (DE)

(73) Assignee: WTW Wissenschaftlich-Technische Werkstaetten GmbH (DE)

( * ) Notice: Subject to any disclaimer, the term of this patent is extended or adjusted under 35 U.S.C. 154(b) by 0 days.

(21) Appl. No.: 09/401,245

(22) Filed: Sep. 23, 1999

(30) Foreign Application Priority Data

Sep. 23, 1998 (DE) .......................................... 198 43 750

(51) Int. Cl.⁷ .............................................. B01D 65/02
(52) U.S. Cl. .................. 436/177; 73/64.56; 73/863.24; 210/85; 210/321.69; 210/411; 210/636; 210/791; 422/61; 436/178
(58) Field of Search ..................... 210/85, 241, 321.69, 210/411, 490, 636, 650, 96.1, 96.2, 739, 483, 321.84, 791; 73/863.23, 863.24; 436/177, 178; 422/61

(56) References Cited

U.S. PATENT DOCUMENTS

| | | | |
|---|---|---|---|
| 3,795,149 A | * | 3/1974 | Gillette et al. |
| 4,501,161 A | | 2/1985 | Endo et al. ............... 73/864.24 |
| 5,221,477 A | * | 6/1993 | Melcher et al. ............. 210/490 |
| 5,505,854 A | | 4/1996 | Glover et al. ............... 210/636 |
| 5,690,830 A | | 11/1997 | Ohtani et al. ............... 210/636 |
| 5,769,539 A | | 6/1998 | Tsang et al. ................ 710/636 |
| 6,306,350 B1 | * | 10/2001 | Mereish et al. ............. 436/177 |

FOREIGN PATENT DOCUMENTS

| | | |
|---|---|---|
| DE | 44 12 284 C1 | 2/1995 |
| EP | 0510328 A2 | 10/1992 |
| JP | 62282263 | 8/1987 |
| JP | 03229129 | 11/1991 |
| WO | WO 97/19026 | 5/1997 |

* cited by examiner

Primary Examiner—Joseph W. Drodge
(74) Attorney, Agent, or Firm—Cantor Colburn LLP

(57) ABSTRACT

The present invention relates to an apparatus and a method for analyzing the amount of chemical substrates in a liquid, more particularly in a clarified solution or a process water. The apparatus comprises a separate filtration housing in which a filter medium is arranged for arresting the filtrate supplied to an analyzer. Provided in the filtration housing is a gas supply means by means of which the filter medium is charged or flushed with a gas.

18 Claims, 2 Drawing Sheets

APPARATUS AND METHOD FOR ANALYZING THE AMOUNT OF CHEMICAL SUBSTRATES IN A LIQUID

BACKGROUND OF THE INVENTION

1. Field of the Invention

The invention relates to an apparatus and a met hod for analyzing the amount of chemical substrates in a liquid, more particularly a clarified solution.

2. Description of Prior Art

In conventional process engineering systems, such as for clarifying waste water by process water treatment plant, for example, it is necessary to check the results of treatment. Treatment quality mainly depends on how high the residual concentration of phosphates, nitrates and ammonium/nitrogen compounds is, remaining in solution. For this purpose use is made of a method of analysis in which the process water is fed to an apparatus comprising a filter unit and an analyzer. Firstly, the process water is passed through the filter unit, more particularly a membrane filter. This membrane filter has the task of holding back solid particles in the process water so that the process water is supplied to the analyzer in a suitable form to enable the concentration of phosphates, nitrates and ammonium/nitrogen compounds to be analyzed. The analyzer is a highly-sensitive measuring instrument connected to further electronic components, this being the reason why it is usually located in a laboratory. Conventionally, the filter medium is located in the process water treatment tank and is connected to the analyzer via a pipe through which the liquid to be analyzed flows. One disadvantage of this existing process configuration is that this pipe is usually very long due to the laboratory being a long way away from the process water treatment tank. When the liquid required for analysis is piped over long distances the concentration of substrates to be analyzed, more particularly phosphates, nitrates and ammonium/nitrogen compounds may change since chemical reactions also take place in this feeder pipe which tend to alter the concentration. Another disadvantage of this existing process configuration is that said feed pipe to the analyzer is usually located outside of a building and thus a heating means needs to be provided, especially in winter, so that the liquid to be analyzed cannot freeze up. The susceptibility of the feed pipe freezing up is also so high because the throughflow capacity of the membrane filter is restricted and only a small amount of the liquid to be analyzed is delivered by the membrane filter. This is why it is necessary to make use of a small pipe diameter which is then, however, even more susceptible to freezing up.

SUMMARY OF THE INVENTION

It is thus the object of the invention to eliminate the disadvantages as described above and to provide a method and an apparatus permitting precise analysis of the amount of chemical substrates in a liquid with no problem.

The gist of the invention is to provide an apparatus having a separate self-contained filtration space making it possible to implement sample treatment separate from the clarifying tank and in the vicinity of the analyzer. As a result of this arrangement said feed pipe for the filtrate to the analyzer can now be maintained as short as possible. The filtration device thus comprises a separate filtration housing to which the process water is fed, and a gas supply means arranged in the filtration housing provided for charging or flushing the filter medium immersed in the liquid with a flow of gas which prevents, or at least delays, the filter medium from clogging up with dirt particles. The process water feed to the filtration housing is made with a volume flow which—as compared to that of the filtration feed—is very high and by means of a pipe dimensioned correspondingly stronger, as a result of which freezing up in winter operation may be effectively avoided. In this arrangement the filtration device is embedded in a circuit in which excess process water is returned back to the process water treatment tank, more particularly to the clarifying tank.

Feeding the filtrate from the filtration device to the analyzer is done either via a very short feed pipe due to the close vicinity of the filtration housing to the analyzer and/or in a temperature-controlled environment, e.g. in an operations building. Accordingly, feeding the filtrate is undisturbed and independent of seasonal changes. The combined effect of the features as described above is an enhanced measuring accuracy. When advantageously making use of a short filtrate feed pipe to the analyzer, chemical reactions in the feed pipe capable of falsifying the chemical substrate concentrations of actual clarifying are avoided.

It is possible in principle to direct a gas flow into the filter medium, In one advantageous aspect the filter medium, more particularly a sheet membrane filter, is arranged above said gas supply means, however, so that the gas bubbles rising to the surface of the membrane produce turbulences resulting in a balance between influent due to filtration and effluent due to turbulences materializing, it being this effluent as just described that is used to control a process which maintains the membranes continually functionable or at least delays clogging up of the filter medium.

For feeding both of the process water into the filtration housing and the filtrate to be analyzed into the analyzer a separate pump may be provided. To save investment costs it is possible to integrate the gas supply means in the frame to which the membrane filter is secured. This is achieved by configuring the lower part of the frame as a gas feeder and providing it with orifices permitting discharge of the gas into the process water in the filtration housing of the filtration means. This gas may be to advantage air since the gas is subject to no further requirements than to create said turbulences at the surface of the membrane. To advantage a blower may be used which introduces the gas into the filtration housing of the filtration means.

In another advantageous aspect of the invention several filter media may be arranged in a single filtration housing to thus increase the effective filter surface and thus the desired filtrate quantity. However, the filter media may also be operated alternatingly to then achieve a more effective cleaning capacity due to the effect of the turbulences of the gas flow on the membrane not operated for arresting the substrate. In addition this also creates the possibility of backwashing the membranes as well as the discharge pipes of these membranes not involved in the filtration function without having to interrupt actual filtration operation.

Advantageously a controller is provided for controlling alternating operation of the filter media between filtration and backwashing.

Should it be necessary to remove the filtration device for mainteance or repair a bypass incorporating a shutoff device is provided connecting the process water feed pipe, so that the liquid may be returned with no problem in bypassing the filtration device. A drain integrated in the system ensures that excess process water together with the arrested solid particles is returned to the clarifying tank. It is thus further assured that the filtration device always receives or discharges a fresh supply of process water and that the liquid to be analyzed has not aged by the time it attains the analyzer.

To ensure simple and reliable control of the complete apparatus a control center may be provided which enables each and every step in the process such as supplying the gas, supplying the process water, piping the liquid to be analyzed, including alternating operation by the aforementioned control unit, to be implemented. This may also be achieved by a controller for the analyzer.

For the method as described to function, making use of sheet membrane filters is not a mandatory requirement, i.e. conventional membrane capillaries or filter media shaped otherwise may also be employed.

BRIEF DESCRIPTION OF THE DRAWINGS

The invention will now be described by way of an example with respect to the schematic figures in which.

DETAILED DESCRIPTION

Figure 1:
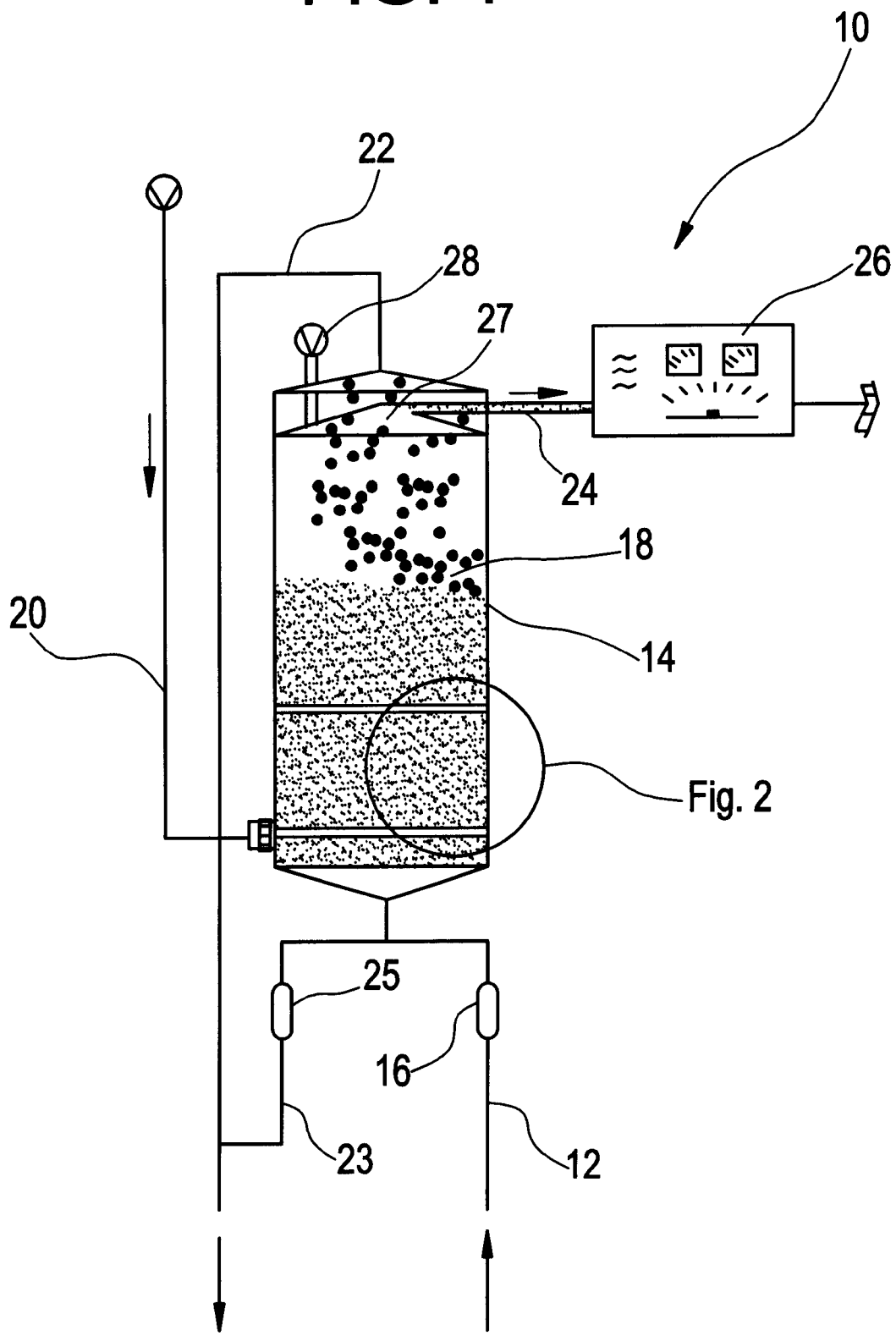
FIG. 1 is a schematic illustration of how a filtration device is configured.

Referring now to FIG. 1 there is illustrated schematically the configuration of the filtration device 10. Feeding the process water is made via the feed pipe 12 into the filtration housing 14. This may be interrupted to advantage via a shutoff device 16 (for example a ball cock) so that the filtration housing may be replaced or serviced with no problem. Accommodated in the housing is the filtration medium, it in this case taking the form of a sheet-type membrane 18. A gas, more particularly air, is supplied to the filtration housing via a gas conduit 20. An overflow 22 looks after removal of the particles arrested by the gas bubbles as well as transporting them upwards with the upflow of the liquid. In addition, the filtration housing 14 may be emptied via a drain 23 porting into the bottom of the filtration housing for maintenance purposes. This drain is shut off by the valve 25 in normal operation. Leading from the filtrate space 27 in the filtration housing 14 to the analyzer is a filtration pipe 24. Likewise connected to the filtrate space 27 is a backwasher 28 capable of charging the filtrate space with a pressurized flow of gas and/or liquid for cleaning the membrane filter 18.

Figure 2:
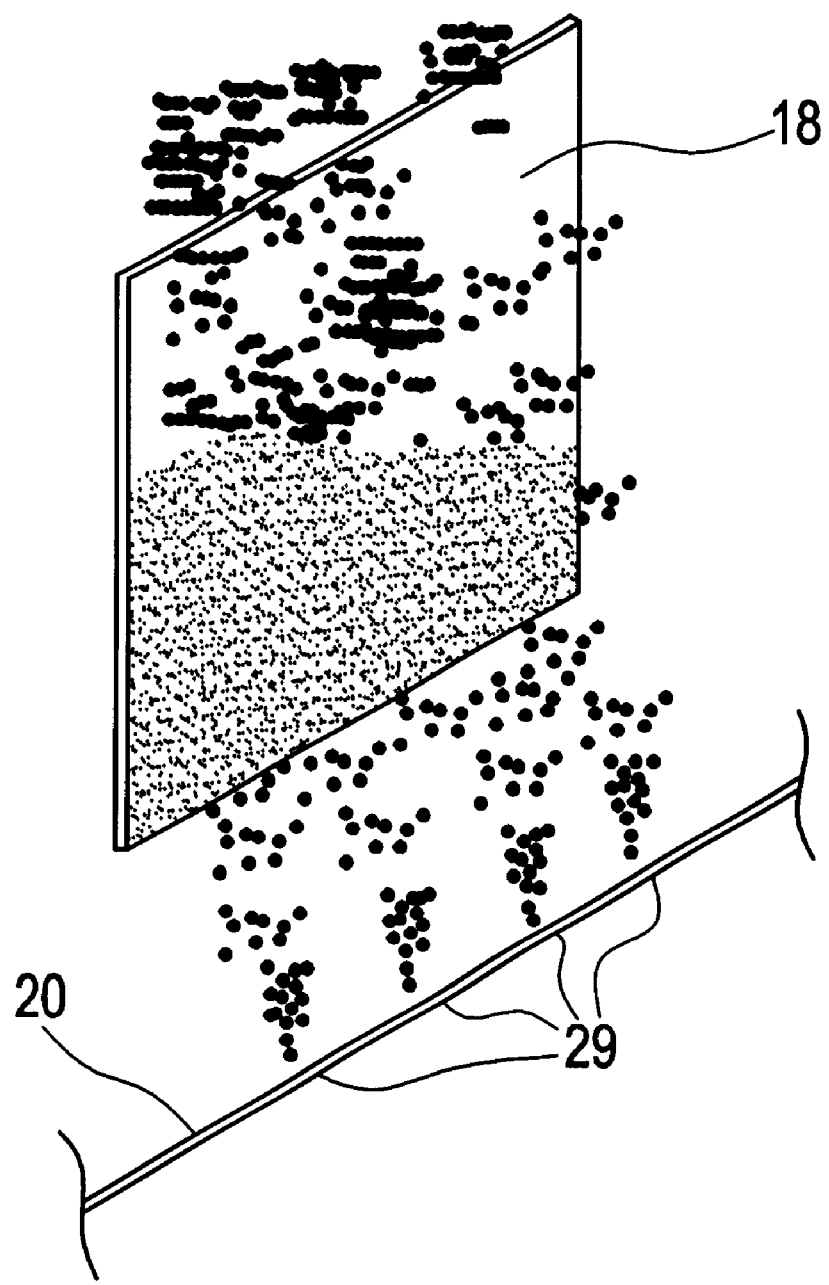
FIG. 2 is a detail taken from FIG. 1 for applying gas to the filter medium.

Referring now to FIG. 2, there is illustrated how the filter medium, configured in this case as a sheet membrane filter 18, receives a charge of gas, the gas thereby flowing from orifices 29 in the gas feed conduit 20 upwards and over the surface of the membrane filter to thus detach soilage from the surface and flush it away upwards.

What is claimed is:

1. An apparatus for analyzing the amount of chemical substrates in a liquid , comprising:

an analyzer;

a filtration device for filtering the liquid to form a filtrate to be fed into said analyzer, cleaned by being charged with gas, said filtration device comprising a separate filtration housing and a filter medium accommodated in said filtration housing separate from said analyzer; and a gas supply means arranged in the filtration housing for discharging the gas into the liquid to be analyzed, so that discharged gas bubbles move along a surface of the filter medium.

2. The apparatus as set forth in claim 1 wherein said filtration device is arranged in the vicinity of said analyzer.

3. The apparatus as set forth in claim 1 wherein said filter medium is configured as a membrane secured to a frame, said membrane being arranged above said gas supply means fitted in a lower part of said filtration housing.

4. The apparatus as set forth in claim 3 wherein said gas supply means comprises a conduit forming a lower part of said frame and orifices for discharging the gas.

5. The apparatus as set forth in claim 1 further comprising a pump for delivering said liquid into said filtration housing.

6. The apparatus as set forth in claim 1 wherein said filter medium is configured in the form of a sheet membrane.

7. The apparatus as set forth in any of the claim 1 wherein said filter medium is configured in the form of membrane capillaries.

8. The apparatus as set forth in claim 1 wherein at least two filter media are arranged in said filtration housing.

9. The apparatus as set forth in claim 8 further comprising a controller for controlling a filtration mode and a backwash mode when said filter media are soiled.

10. The apparatus as set forth in claim 1 further comprising a pressuring means connected as a backwasher to a filtrate space of said filtration device.

11. The apparatus as set forth in claim 10 further comprising a controller for controlling a filtration mode and a backwash mode when said filter media are soiled.

12. The apparatus as set forth in claim 10 wherein said pressuring means includes a pump.

13. The apparatus as set forth in claim 1 further comprising a drain for removing said liquid from said filtration housing including an inlet port porting into a bottom of said filtration housing and a shutoff device.

14. The apparatus as set forth in claim 1 further comprising a process controller for controlling said gas supply means, a feed rate of said liquid, a deliver of said filtrate to said analyzer, and an operation of said analyzer.

15. A method for analyzing the amount of chemical substrates in a liquid, comprising:

filtering said liquid using a filtration device including a separate filtration housing and a filter medium accommodated in said filtration housing;

supplying a filtrate to an analyzer separate from said filtration housing; and supplying gas into the liquid to be analyzed, so that discharged gas bubbles move along a surface of said filter medium.

16. The method as set forth in claim 15 wherein at least two filter media are arranged in said filtration housing.

17. The method as set forth in claim 16 further comprising backwashing said filter media to remove residues.

18. The method as set forth in claim 16 wherein at least one of said filter media are operated in a filtration mode while at least one of said media are operated in a backwash mode.

* * * * *